(12) United States Patent
Choi et al.

(10) Patent No.: US 9,398,857 B2
(45) Date of Patent: Jul. 26, 2016

(54) DIAGNOSTIC IMAGING APPARATUS AND METHOD OF OPERATING THE SAME

(71) Applicant: Samsung Medison Co., Ltd., Gangwon-do (KR)

(72) Inventors: Sung-jin Choi, Gangwon-do (KR); Jong-sik Kim, Gangwon-do (KR); Yoon-chang Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 587 days.

(21) Appl. No.: 13/711,255

(22) Filed: Dec. 11, 2012

(65) Prior Publication Data
US 2013/0169782 A1 Jul. 4, 2013

(30) Foreign Application Priority Data
Jan. 4, 2012 (KR) .................. 10-2012-0001148

(51) Int. Cl.
*A61B 8/00* (2006.01)
*A61B 5/00* (2006.01)
*A61B 8/08* (2006.01)
(Continued)

(52) U.S. Cl.
CPC ............... *A61B 5/0077* (2013.01); *A61B 8/085* (2013.01); *A61B 8/469* (2013.01); *A61B 8/481* (2013.01); *A61B 8/5223* (2013.01); *G01R 33/5608* (2013.01); *A61B 8/0891* (2013.01); *G01R 33/5635* (2013.01)

(58) Field of Classification Search
CPC .... A61B 5/0077; A61B 8/085; A61B 8/0891; A61B 8/469; A61B 8/481; A61B 8/5223; G01R 33/5608; G01R 33/5635

USPC ............. 347/77; 382/128; 600/300, 407, 411, 600/431, 437, 440, 443, 458

See application file for complete search history.

(56) References Cited

U.S. PATENT DOCUMENTS 6,540,680 B1 * 4/2003 Kurosaki ............... A61B 8/463
600/443
7,024,024 B1 * 4/2006 Aiazian .................. A61B 8/461
382/128

(Continued)

FOREIGN PATENT DOCUMENTS

JP 6-269424 A 9/1994
JP 2005-137558 A 6/2005

(Continued)

OTHER PUBLICATIONS

Korean Notice of Final Rejection issued in counterpart Korean Patent Application No. 10-2012-0001148 on Nov. 21, 2014; 5 pages, with English translation.

(Continued)

*Primary Examiner* — Thai Tran
*Assistant Examiner* — Stephen Smith
(74) *Attorney, Agent, or Firm* — McDermott Will & Emery LLP

(57) ABSTRACT

A diagnostic imaging apparatus and a method of operating the diagnostic imaging apparatus. The diagnostic imaging apparatus includes: a probe that scans a subject, into which a contrast agent is injected, to obtain a scan signal; and a display unit that displays a scan video image obtained based on the scan signal, on a first region of a screen, and N captured images from the scan video image on a second region of the screen, where N is a natural number.

18 Claims, 9 Drawing Sheets

(51) Int. Cl.
*G01R 33/56* (2006.01)
*G01R 33/563* (2006.01)

(56) References Cited

U.S. PATENT DOCUMENTS

| | | | | |
|---|---|---|---|---|
| 8,520,927 | B2* | 8/2013 | Satoh | G06T 7/0016 382/128 |
| 2004/0066957 | A1* | 4/2004 | Miller | A61B 8/463 382/128 |
| 2005/0033123 | A1* | 2/2005 | Gardner | G06T 7/0016 600/300 |
| 2005/0033179 | A1* | 2/2005 | Gardner | A61B 8/0883 600/458 |
| 2007/0055161 | A1* | 3/2007 | Garg | A61B 8/06 600/458 |
| 2007/0167761 | A1 | 7/2007 | Hashimoto | |
| 2008/0081998 | A1* | 4/2008 | Pan | A61B 8/13 600/458 |
| 2009/0054775 | A1 | 2/2009 | Kato et al. | |
| 2010/0081938 | A1 | 4/2010 | Kato | |
| 2010/0246909 | A1* | 9/2010 | Blum | A61B 5/055 382/128 |
| 2012/0027282 | A1* | 2/2012 | Yoshikawa | A61B 8/06 382/131 |
| 2013/0090548 | A1* | 4/2013 | Hamilton | A61B 5/004 600/411 |

FOREIGN PATENT DOCUMENTS

| | | |
|---|---|---|
| JP | 2007-082649 A | 4/2007 |
| JP | 2007-151972 A | 6/2007 |
| JP | 2009-045276 A | 3/2009 |
| JP | 2010-075586 A | 4/2010 |
| JP | 2010-094237 A | 4/2010 |
| JP | 2010-158360 A | 7/2010 |

OTHER PUBLICATIONS

Korean Notice of Allowance issued in counterpart Korean Patent Application No. 10-2012-0001148 on Dec. 17, 2014; 7 pages with English translation.
Korean Office Action issued in Korean Application No. 10-2012-001148 dated May 30, 2014, w/English translation.
Extended European Search Report issued in Eropean Application No. 12161833.4 mailed Jun. 4, 2013.
Averkiou et al., "Quantification of tumor microvascularity with respiratory gated contrast enhanced ultrasound for monitoring therapy", Ultrasound in Med & Bio., vol. 36, No. 1, Jan. 2010, pp. 68-77.
Yang et al., "Cone Beam CT tumor vasculature dynamic study (Murine nodel)", Medical Imaging 2008: Physiology, Function and Structure from Medical Images, vol. 6916, (2008), pp. 691629-1-691629-8.

* cited by examiner

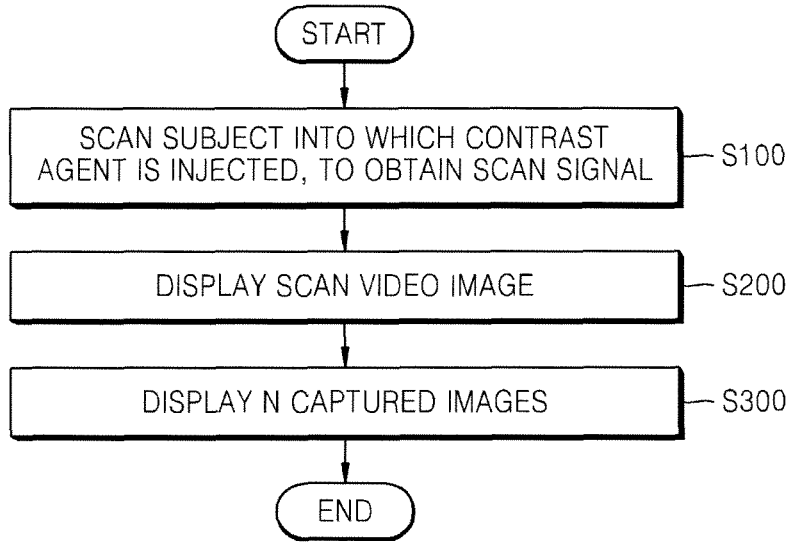
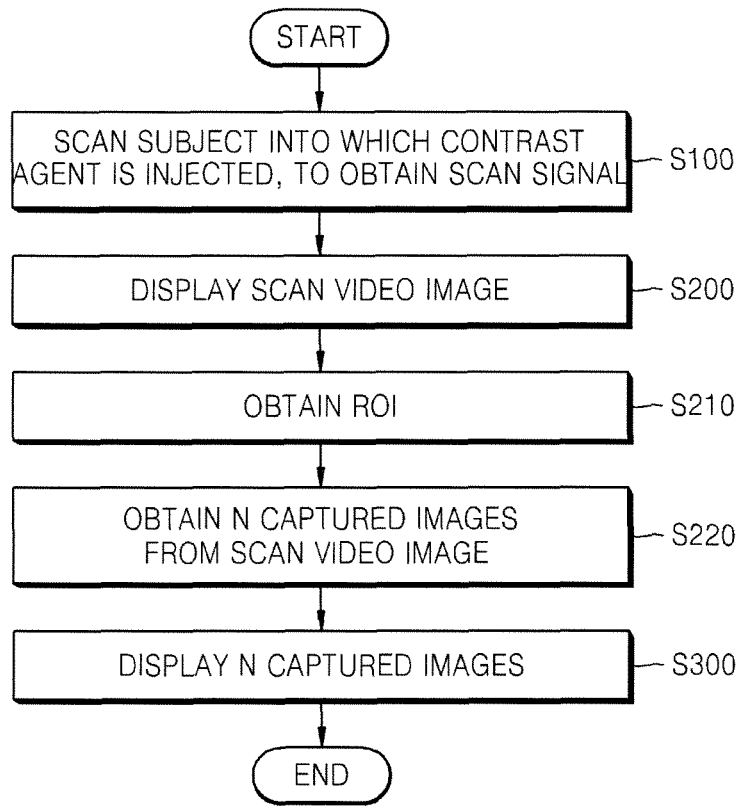

DIAGNOSTIC IMAGING APPARATUS AND METHOD OF OPERATING THE SAME

CROSS-REFERENCE TO RELATED PATENT APPLICATION

This application claims the benefit of Korean Patent Application No. 10-2012-0001148, filed on Jan. 4, 2012, in the Korean Intellectual Property Office, the disclosure of which is incorporated herein in its entirety by reference.

BACKGROUND OF THE INVENTION

1. Field of the Invention

The present invention relates to a diagnostic imaging apparatus and a method of operating the same.

2. Description of the Related Art

A diagnostic imaging apparatus may be, for example, a medical imaging apparatus such as an ultrasonic imaging apparatus, a computer tomography (CT) system, or a magnetic resonance imaging (MRI) system.

By using the diagnostic imaging apparatus, a subject into which a contrast agent is injected may be scanned to obtain a contrast agent image, and the contrast agent image may be displayed. A user may diagnose an illness of the subject by viewing the contrast agent image.

The contrast agent injected into the subject moves along blood vessels of the subject. The blood vessels shown on the contrast agent image become bright as the contrast agent flows into the blood vessels, and become dark when the contrast agent flows away therefrom. Cancer tissues create a large number of blood vessels around themselves to draw a large amount of blood, and thus the contrast agent quickly flows into and out from the cancer tissues compared to normal tissues. Accordingly, a user may diagnose the presence of cancer tissues in the subject by determining changes in brightness of the contrast agent image over time.

However, although it ma be possible for the user to diagnose cancer just by viewing a contrast agent image that is displayed in real-time after the contrast agent is injected into the subject, it is difficult for the user to easily recognize the change in brightness in the contrast agent image according to time. Accordingly, diagnosis accuracy may decrease. To increase diagnosis accuracy, an additional process such as rechecking of the contrast agent image by the user may be performed. However, if the additional process is performed, diagnosis may be delayed.

Thus, an efficient diagnostic imaging apparatus and a method of operating the same efficiently are required.

SUMMARY OF THE INVENTION

The present invention provides an efficient diagnostic imaging apparatus and a method of operating the apparatus efficiently.

According to an aspect of the present invention, there is provided a diagnostic imaging apparatus, comprising: a probe that scans a subject into which a contrast agent is injected, to obtain a scan signal; and a display unit that displays a scan video image obtained based on the scan signal, on a first region of a screen, and N captured images from the scan video image on a second region of the screen, where N is a natural number.

The display unit may display a reference time-intensity curve which is a time-intensity curve of a region of interest (ROI) in the scan video image, on the first region.

The display unit may display N marker time-intensity curves respectively corresponding to the N captured images on the second region, and each of the N marker time-intensity curves may indicate capture time point or capture time section of a corresponding captured image among the N captured images based on the reference time-intensity curve.

The N captured images may be obtained based on a user request.

The diagnostic imaging apparatus may further comprise a control unit that divides the scan video image into N phases based on the reference time-intensity curve, and captures the scan video image from each of the N phases to obtain the N captured images.

The ROI is obtained based on a user request.

The diagnostic imaging apparatus further comprise a control unit that divides the scan video image into a plurality of divided regions, obtains a plurality of divided time-intensity curves which are respectively time-intensity curves of the plurality of divided regions, and obtains M groups based on the plurality of divided time-intensity curves, wherein the M groups each include at least one among the plurality of divided regions, and M is a natural number.

The display unit may display the M groups on the scan video image.

The display unit may display a group time-intensity curve including a time-intensity curve of each of the M groups, on the first region.

The display unit may display N marker time-intensity curves respectively corresponding to the N captured images, on the second region, and each of the N marker time-intensity curves may indicate capture time point or capture time section of a corresponding captured image among the N captured images based on the reference time-intensity curve.

The N captured images may be obtained based on a user request.

The control unit may divide the scan video image into N phases based on the group time-intensity curve, and capture the scan video image from each of the N phases to obtain the N captured images.

According to another aspect of the present invention, there is provided a method of operating a diagnostic imaging apparatus, the method comprising: scanning a subject, into which a contrast agent is injected, to obtain a scan signal; displaying a scan video image that is obtained based on the scan signal, on a first region of a screen; and displaying N captured images captured from the scan video image, on a second region of the screen, where N is a natural number.

According to another aspect of the present invention, there is provided a computer-readable recording medium having embodied thereon a program for implementing the method of operating a diagnostic imaging apparatus described above.

BRIEF DESCRIPTION OF THE DRAWINGS

The above and other features and advantages of the present invention will become more apparent by describing in detail exemplary embodiments thereof with reference to the attached drawings in which:

FIG. 12 is a flowchart illustrating a method of operating a diagnostic imaging apparatus according to another embodiment of the present invention;

FIG. 13 is a flowchart illustrating a method of operating a diagnostic imaging apparatus according to another embodiment of the present invention;

DETAILED DESCRIPTION OF THE INVENTION

Hereinafter, preferred embodiments of the present invention will be described with reference to the attached drawings. As used herein, the term "and/or" includes any and all combinations of one or more of the associated listed items. Expressions such as "at least one of," when preceding a list of elements, modify the entire list of elements and do not modify the individual elements of the list.

Figure 1:
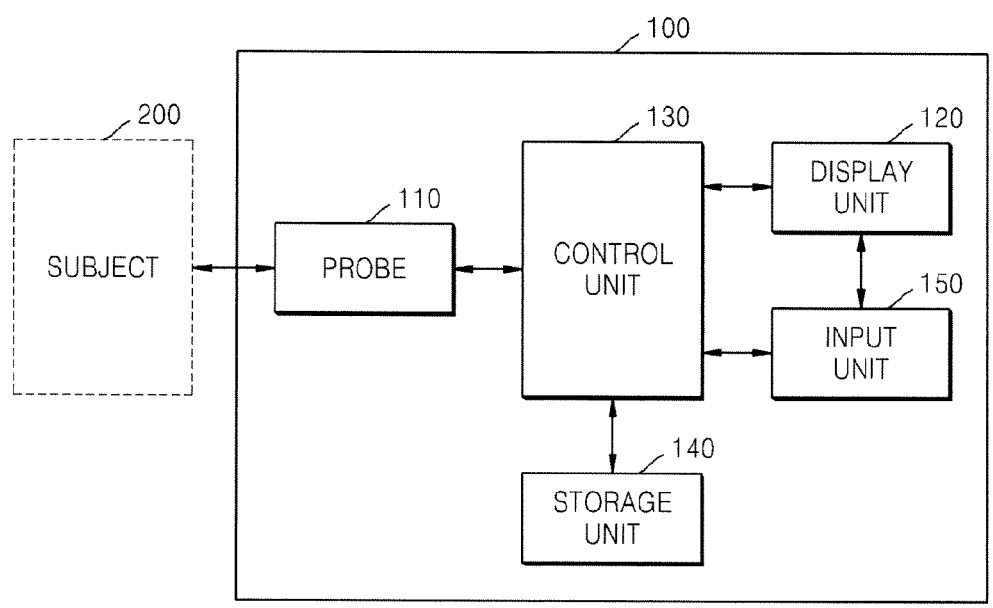
FIG. 1 is a block diagram illustrating a diagnostic imaging apparatus according to an embodiment of the present invention.

FIG. 1 is a block diagram illustrating a diagnostic imaging apparatus 100 according to an embodiment of the present invention.

Referring to FIG. 1, the diagnostic imaging apparatus 100 includes a probe 110 and a display unit 120. The diagnostic imaging apparatus 100 may further include a control unit 130, a storage unit 140, and an input unit 150.

The diagnostic imaging apparatus 100 may be a medical imaging apparatus such as an ultrasonic imaging apparatus, a computer tomography (CT) system, or a magnetic resonance imaging (MRI) system.

The probe 110 scans a subject 200, into which a contrast agent is injected, to obtain a scan signal. The subject 200 may be an animal body including a human body or a part of an animal body.

The display unit 120 displays a scan video image obtained based on the scan signal, in a first region of a screen. Also, the display unit 120 may display N captured images that are captured from a scan video image in a second region of the screen. N is a natural number.

The control unit 130 may control operations of the probe 110, the display unit 120, and the storage unit 140 to control the overall operation of the diagnostic imaging apparatus 100. The control unit 130 may obtain a scan video image based on a scan signal. In addition, the control unit 130 may capture the scan video image to obtain N captured images.

The storage unit 140 may store the scan video image and the N captured images. The input unit 150 may receive a user request from a user and transmit the same to the control unit 130. The control unit 130 may control an operation of the diagnostic imaging apparatus 100 based on the user request. The input unit 150 or a portion of the input unit 150 may be displayed on the display unit 120.

Figure 2:
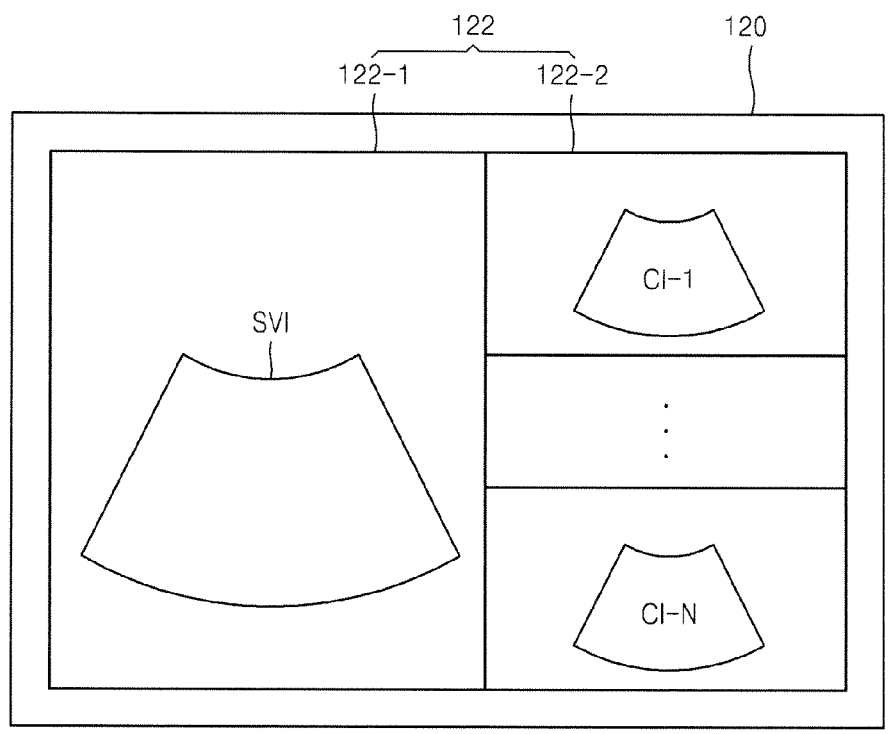
FIG. 2 is a schematic view of a screen of a display unit of FIG. 1 according to an embodiment of the present invention.

FIG. 2 is a schematic view of a screen 122 of the display unit 120 of FIG. 1 according to an embodiment of the present invention.

Referring to FIG. 2, the screen 122 of the display unit 120 may include a first region 122-1 and a second region 122-2. A scan video image SVI obtained based on a scan signal may be displayed on the first region 122-1. N captured images CI-1, . . . , CI-N captured from the scan video image SVI may be displayed on the second region 122-2. The second region 122-2 may include N sub-regions.

Referring to FIGS. 1 and 2, the display unit 120 may display the scan video image SVI in real-time, simultaneously with scanning the subject 200. To display the scan video image SVI in real-time, the control unit 130 may process a scan signal obtained from the probe 110 in real-time, thereby obtaining a scan video image SVI.

Alternatively, the display unit 120 may display a scan video image SVI stored in the storage unit 140 upon a user request after the subject 200 is scanned. The input unit 150 may receive from a user a user request to output the scan video image SVI.

The N captures images CI-1, . . . , CI-N may be still images that are captured at different time points in an output section of the scan video image SVI or video images captured in different time sections in an output section of the scan video image SVI. An n-th captured image CI-n (n=1, 2, . . . , N) may be a still image that is captured at an n-th capture time point in an output section of the scan video image SVI or a video image that is captured in an n-th capture time section in an output section of the scan video image SVI. If the n-th captured image CI-n is a video image, the display unit 120 may repeat outputting of the n-th captured image CI-n until outputting of the scan video image SVI is completed.

The display unit 120 may align and display the N captured images CI-1, . . . , CI-N in the second region 122-2 in the order of capture time points or in the order of capture time sections.

Figure 3:
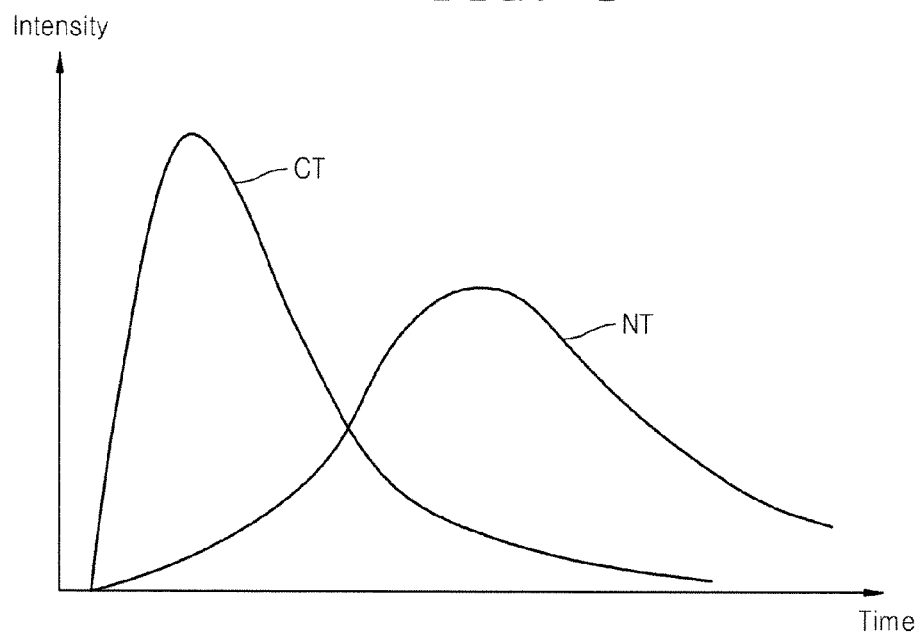
FIG. 3 is a time-intensity curve of a scan video image according to an embodiment of the present invention.

FIG. 3 is a time-intensity curve of a scan video image SVI according to an embodiment of the present invention.

Referring to FIG. 3, an x-axis denotes time, and a y-axis denotes intensity. The time-intensity curve of FIG. 3 includes a cancer tissue time-intensity curve CT which is a time-intensity curve of a portion of the scan video image SVI of FIG. 2 where cancer tissue is shown, and a normal tissue time-intensity curve NT which is a time-intensity curve of a portion of the scan video image SVI of FIG. 2 where normal tissues is shown.

The contrast agent injected into the subject 200 of FIG. 1 moves along blood vessels thereof. A portion of the scan video image SVI where blood vessels are shown becomes bright as the contrast agent flows into the blood vessels, and when the contrast agent flows out from the blood vessels, the portion becomes dark.

Cancer tissues create a large number of blood vessels around themselves to draw a large amount of blood, and thus the contrast agent quickly flows into and out from the cancer tissues compared to normal tissues. Accordingly, in the cancer tissue time-intensity curve CT, intensity is quickly raised and then quickly decreases compared to the normal tissue time-intensity curve NT.

Thus, if there is a portion which quickly brightens and then quickly darkens thereafter in the scan video image SVI, the portion may be diagnosed as cancer tissue. As such, by determining changes in brightness of the scan video image SVI according to time, the user may diagnose cancer tissue in the subject 200.

Referring to FIGS. 1 and 2 again, the user may diagnose cancer tissue in the subject 200 by viewing the scan video image and N captured images CI-1, . . . , CI-N displayed on the display unit 120. When the display unit 120 aligns the N captured images CI-1, . . . , CI-N according to the order of capturing time points or according to the order of capture time sections, the user may view a brightness change according to time at a glance through the N captured images CI-1, . . . , CI-N. Consequently, the user may easily determine a brightness change in the scan video image according to time.

If only the scan video image SVI is displayed on the display unit 120, the user may not easily recognize a brightness change in the scan video image SVI according to time. Thus, diagnosis accuracy may decrease. To increase diagnosis accuracy, an additional process such as rechecking of the scan video image SVI by the user may be performed. However, if the additional process is performed, time for diagnosis may be delayed.

Accordingly, according to the diagnostic imaging apparatus 100 of the current embodiment of the present invention, user convenience may be provided in diagnosis. In addition, diagnosis speed may be improved by using the diagnostic imaging apparatus 100.

Figure 4:
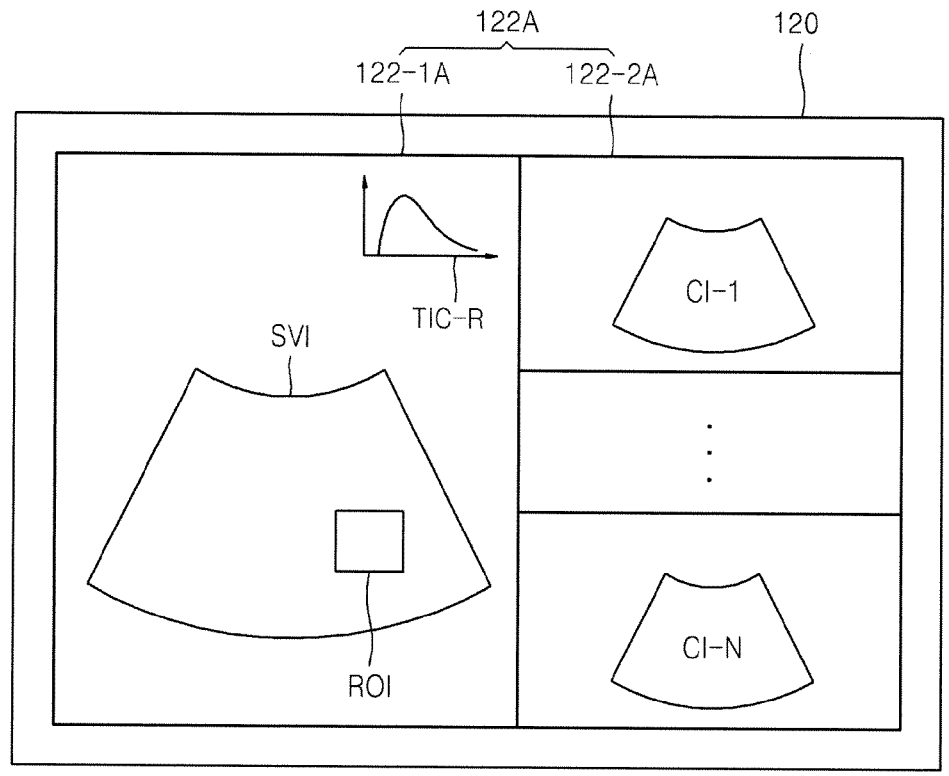
FIG. 4 is a schematic view of a screen of a display unit of FIG. 1 according to another embodiment of the present invention.

FIG. 4 is a schematic view of a screen 122A of the display unit 120 of FIG. 1 according to another embodiment of the present invention. The description of the screen 122 of FIG. 2 may be applied to the screen 122A of FIG. 4, and thus, the following description will focus on differences from the screen 122 of FIG. 2.

Referring to FIG. 4, the screen 122A of the display unit 120 may include a first region 122-1A and a second region 122-2A. A scan video image is displayed on the first region 122-1A. N captured images CI-1, . . . , CI-N that are captured from the scan video image SVI are displayed on the second region 122-2A.

A region of interest (ROI) may be displayed on the scan video image SVI. The ROI may be displayed based on a user request. The user request may be input via the input unit 150. Alternatively, the ROI may be selected by the control unit 130 and displayed irrespective of a user request. A method in which the control unit 130 selects a ROI irrespective of a user request will be described later.

A reference time-intensity curve TIC-R which is a time-intensity curve of a ROI may be displayed on the first region 122-1A. When the user determines whether a ROI is a cancer tissue or not, the reference time-intensity curve TIC-R may provide objective standards in terms of diagnosing. Thus, diagnosis accuracy may be increased.

Figure 5:
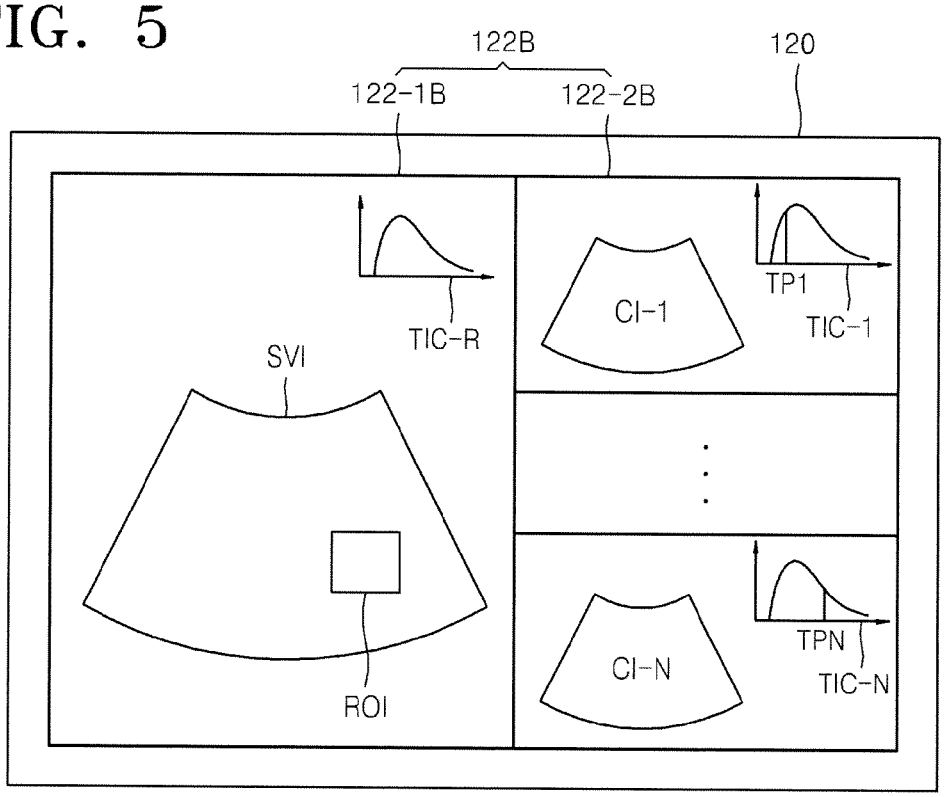
FIG. 5 is a schematic view of a screen of a display unit of FIG. 1 according to another embodiment of the present invention.

FIG. 5 is a schematic view of a screen 122B of the display unit 120 of FIG. 1 according to another embodiment of the present invention. The description of the screen 122 of FIG. 2 and the screen 122A of FIG. 4 may be applied to the screen 122B of FIG. 5, and thus, the following description will focus on differences from the screen 122 of FIG. 2 and the screen 122A of FIG. 4.

Referring to FIG. 5, the screen 122B of the display unit 120 may include a first region 122-1B and a second region 122-2B. In the second region 122-2B, N marker time-intensity curves TIC-1, . . . , TIC-N respectively corresponding to the N captured images CI-1, . . . , CI-N may be displayed.

Each of the N marker time-intensity curves TIC-1, . . . , TIC-N shows capture time point of a corresponding captured image among the n captured images CI-1, . . . , CI-N based on the reference time-intensity curves TIC-R. For example, n marker time-intensity curves TIC-n (n=1, 2, . . . , N) show a capture time point TPn of an n-th captured image CI-n on the reference time-intensity curve TIC-R.

The user may intuitively perceive the capture time points TP1, . . . , TPN of the N captured images CI-1, . . . , CI-N by viewing the N marker time-intensity curves TIC-1, . . . , TIC-N. Accordingly, diagnosis convenience may be provided, and diagnosis accuracy may be increased.

Figure 6:
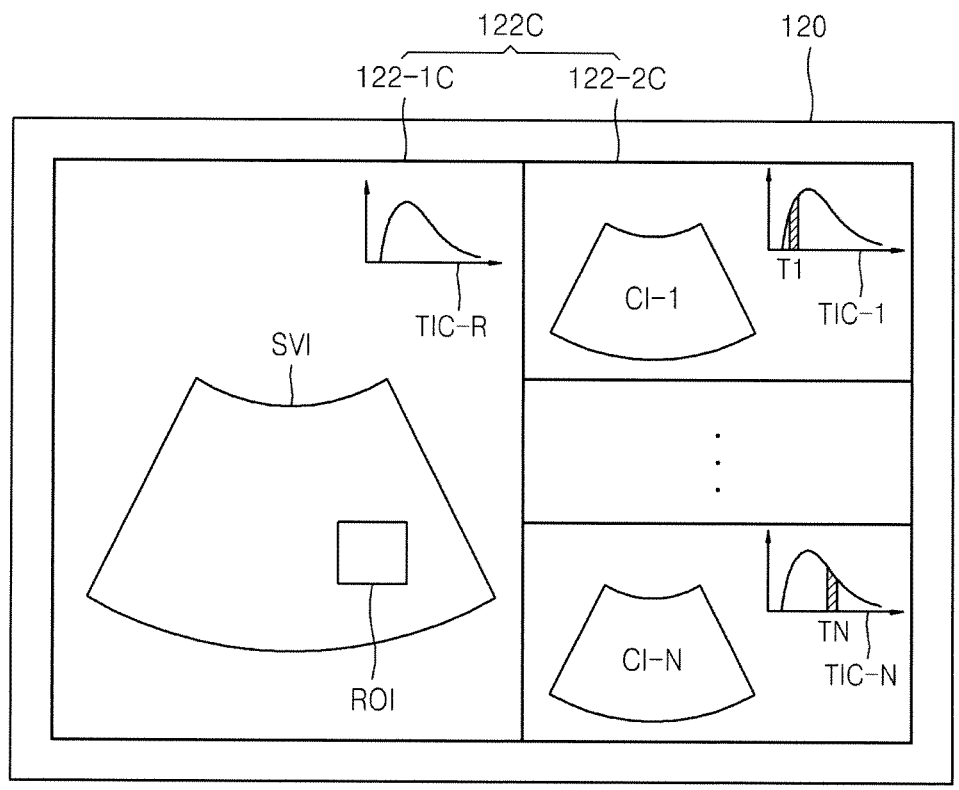
FIG. 6 is a schematic view of a screen of a display unit of FIG. 1 according to another embodiment of the present invention.

FIG. 6 is a schematic view of a screen 122C of the display unit 120 of FIG. 1 according to another embodiment of the present invention. The description of the screen 122B of FIG. 5 may be applied to the screen 122C of FIG. 6, and thus, the following description will focus on differences from the screen 122B of FIG. 5.

Referring to FIG. 6, the screen 122C of the display unit 120 may include a first region 122-1C and a second region 122-2C. Each of the N marker time-intensity curves TIC-1, . . . , TIC-N displayed on the second region 122-2C may show capture time section of a corresponding captured image among N captured images CI-1, . . . , CI-N based on reference time-intensity curves TIC-1, . . . , TIC-N. For example, an n-th marker time-intensity curves TIC-n (n=1, 2, . . . , N) shows a capture time section Tn of an n-th captured image CI-n on the reference time-intensity curve TIC-R.

Referring to FIG. 1 again, the display unit 120 may simultaneously display a scan video image SVI and N captured images CI-1, . . . , CI-N that are captured from the scan video image SVI as illustrated in FIGS. 2, 4, and 6.

The N captured images CI-1, . . . , CI-N may be obtained upon user request. The user request may be input via the input unit 150.

At the same time as viewing the scan video image SVI (see FIGS. 2, 4, and 6) displayed on the display unit 120, the user may input a user request regarding a capture time point or a capture time section, to the input unit 150. For example, the control unit 130 may capture a frame of a scan video image that is output at a time point when the user request is input, as a captured image. For another example, the user may input a user request regarding a capture time point or a capture time section on the reference time-intensity curve TIC-R (see FIGS. 4 through 6) displayed on the display unit 120.

The control unit 130 may capture the scan video image SVI based on the user request regarding a capture time point or a capture time section, thereby obtaining N captured images CI-1, . . . , CI-N.

Alternatively, N captured images CI-1, . . . , CI-N may be captured by using the control unit 130 irrespective of a user request. For example, the control unit 130 may periodically capture a scan video image SVI to obtain N captured images CI-1, . . . , CI-N. For another example, the control unit 130 may obtain N captured images CI-1, . . . , CI-N based on a time-intensity curve of a ROI.

Figure 7:
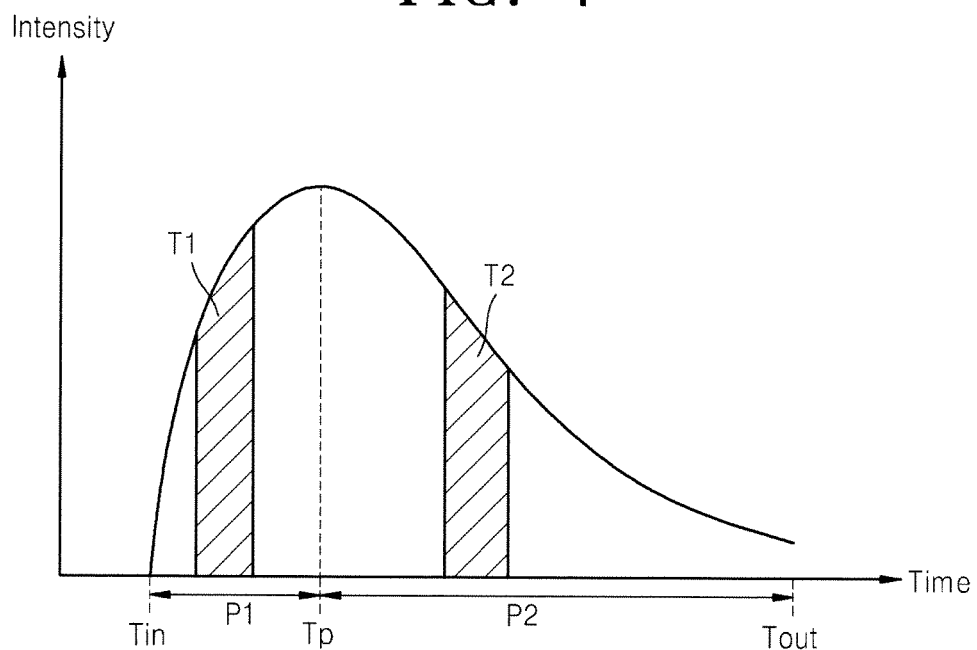
FIG. 7 is a time-intensity curve of a region of interest (ROI) of a scan video image according to an embodiment of the present invention.

FIG. 7 is a time-intensity curve of a ROI of a scan video image according to an embodiment of the present invention.

Referring to FIGS. 1 and 7, the control unit 130 may divide a scan video image SVI into N phases based on a time-intensity curve of a ROI. Here, N is a natural number.

The control unit 130 may obtain a reference time point from the time-intensity curve in order to divide a scan video image into N phases. For example, the reference time point may include a starting point Tin, a peak point Tp, and an end point Tout.

The control unit 130 may divide a scan video image into a first phase P1 from the starting point Tin to the peak point Tp and a second phase P2 from the peak point Tp to the end point Tout as illustrated in FIG. 7. The first phase P1 is also referred to as a wash-in phase, and the second phase P2 is referred to as a wash-out phase.

In FIG. 7, N is 2, and N phases are divided as the first phase P1 and the second phase P2, but the embodiments of the present invention are not limited to FIG. 7. N phases may include an arterial phase, a portal vein phrase, and a late phase. Alternatively, if Sonazoid is used as a contrast agent, N phases may include an arterial phase, a portal vein phase, a late phase, and a Kupffer phase.

The control unit 130 may select capture time sections T1 and T2 from each of N phases, that is, the first and second phases P1 and P2, and may capture a scan video image SVI from the capture time sections T1 and T2 to obtain N captured images. While the capture time sections T1 and T2 are selected from each of N phases P1 and P2 in FIG. 7, the control unit 130 may also select capture time points from each of N phases P1 and P2.

As described above, the control unit 130 may capture a scan video image from each of N phases P1 and P2 to obtain N captured images.

Hereinafter, a method of selecting a ROI irrespective of a user request by using the control unit 130 will be described.

Figure 8:
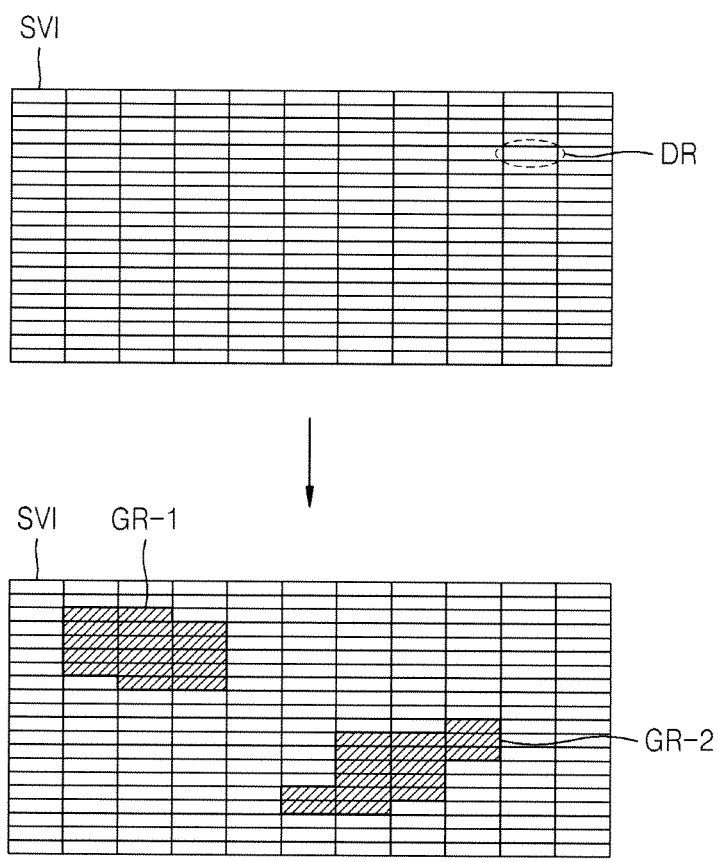
FIG. 8 is a schematic view illustrating an operation in which a ROI is obtained from a scan video image, according to an embodiment of the present invention.

FIG. 8 is a schematic view illustrating an operation in which a ROI is obtained from a scan video image, according to an embodiment of the present invention.

Referring to FIGS. 1 and 8, the control unit 130 may divide a scan video image SVI into a plurality of divided regions DR. The plurality of divided regions DR may each include at least one pixel. The control unit 130 may obtain a plurality of divided time-intensity curves respectively corresponding to the plurality of divided regions DR. The control unit 130 may obtain M groups based on the plurality of divided time-intensity curves, and may obtain M groups as ROIs. M groups may each include at least one of the plurality of divided regions DR. Here, M is a natural number. While with regard to FIG. 8, M is 2, and the M groups include a first group GR-1 and a second group GR-2, the embodiments of the present invention are not limited to FIG. 8.

The control unit 130 may group divided regions DR having similar divided time-intensity curves among the plurality of divided regions DR to obtain M groups GR-1 and GR-2. The control unit 130 may obtain a reference time point for each of the plurality of divided time-intensity curves. For example, the reference time point may include the starting point Tin, the peak point Tp, and the end point Tout (see FIG. 7). The control unit 130 may exclude divided regions DR from which a reference time point is not detected when obtaining the M groups GR-1 and GR-2. For example, among the plurality of divided regions DR, the control unit 130 may exclude those divided regions DR, from which the starting point Tin (see FIG. 7) or the end point Tout (see FIG. 7) is not detected.

The control unit 130 may determine those divided time-intensity curves whose reference time points differ by a critical value or less, as similar, among the plurality of divided time-intensity curves. The critical value may be variously set, for example, upon a user request or using statistical methods.

The control unit 130 may group divided regions having similar divided time-intensity curves to thereby obtain M groups GR-1 and GR-2.

Next, a method of obtaining the starting point Tin and the end point Tout (see FIG. 7) of a divided time-intensity curve using the control unit 130 according to an embodiment of the present invention will be described.

The control unit 130 may obtain an average intensity of an initial scan image obtained when a contrast agent is injected into the subject 200, as a baseline. For example, the initial scan image may be a first frame of the scan video image SVI (see FIG. 2) including a plurality of frames.

In addition, the control unit 130 may obtain a cumulative gradient curve from each of the plurality of divided regions DR based on the plurality of divided time-intensity curves. The cumulative gradient curve is obtained by accumulating differences in intensities of frames.

If there is a time point at which an intensity increases from 0 on a cumulative gradient curve of each of the divided regions DR, the control unit 130 may detect the time point as a starting point Tin (see FIG. 7). Average intensity of the divided regions DR at the staring point Tin may be greater than the average intensity of the baseline.

If there is a time point at which an intensity continuously decreases after the starting point Tin (see FIG. 7) on a cumulative gradient curve of each of the divided regions DR to finally reach 0, the control unit 130 may detect the time point where 0 is reached as the end point Tout (see FIG. 7). The average intensity of the divided regions DR at the end point Tout (see FIG. 7) may be smaller than the average intensity on the baseline.

Figure 9:
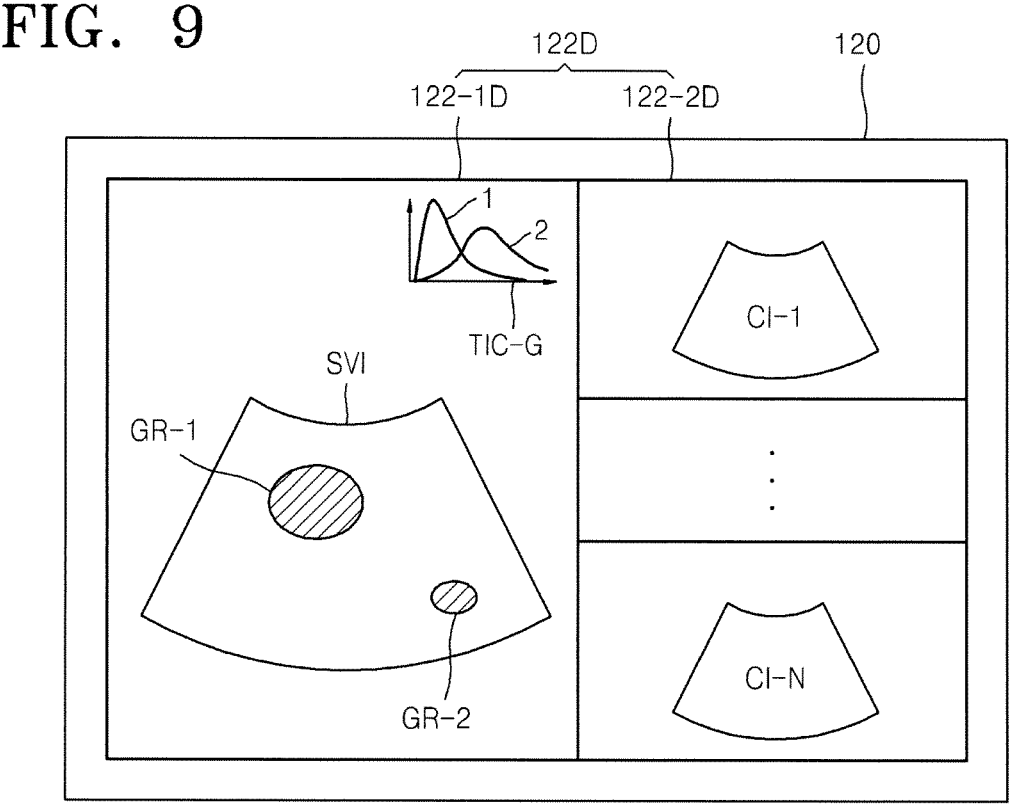
FIG. 9 is a schematic view of a screen of a display unit of FIG. 1 according to another embodiment of the present invention.

FIG. 9 is a schematic view of a screen 122D of the display unit 120 of FIG. 1 according to another embodiment of the present invention. The description of the screen 122 of FIG. 2 may be applied to the screen 122D of FIG. 9, and thus, the following description will focus on differences from the screen 122 of FIG. 2.

Referring to FIGS. 1 and 9, the screen 122D of the display unit 120 may include a first region 122-1D and a second region 122-2D. The display unit 120 may display M groups GR-1 and GR-2 that are obtained as ROIs by the control unit 130 from a scan video image SVI displayed on the first region 122-1D. The M groups GR-1 and GR-2 may be displayed on a scan video image SVI based on colors. For example, the first group GR-1 or an outer line of the first group GR-1 may be marked red on the scan video image SVI, and the second group GR-2 or an outer line of the second group GR-2 may be marked blue on the scan video image SVI. However, this is merely an example, and the display unit 120 may mark M groups GR-1 and GR-2 on the scan video image SVI in various ways.

Also, a group time-intensity curve TIC-G including time-intensity curves 1 and 2 of each of the M groups GR-1 and GR-2 may be displayed on the first region 122-1D.

Figure 10:
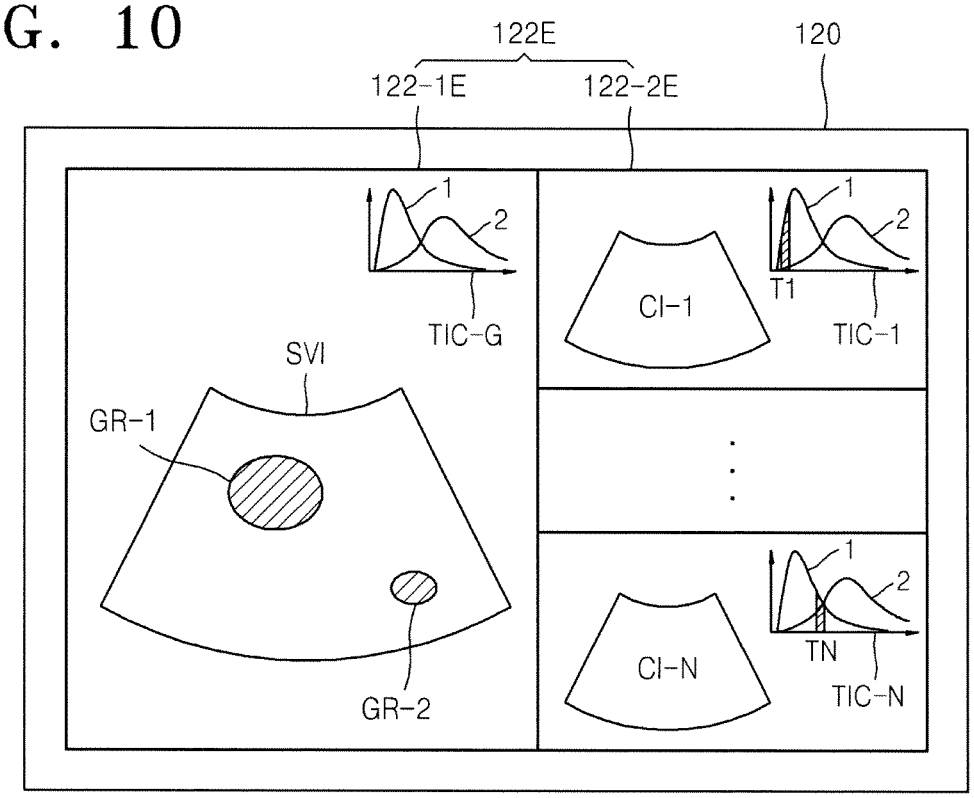
FIG. 10 is a schematic view of a screen of a display unit of FIG. 1 according to another embodiment of the present invention.

FIG. 10 is a schematic view of a screen 122E of the display unit 120 of FIG. 1 according to another embodiment of the present invention. The description of the screen 122 of FIG. 2 and the screen 122D of FIG. 9 may be applied to the screen 122E of FIG. 10, and thus, the following description will focus on differences from the screen 122 of FIG. 2 and the screen 122D of FIG. 9.

Referring to FIG. 10, the screen 122E of the display unit 120 may include a first region 122-1E and a second region 122-2E. In the second region 122-2E, N marker time-intensity curves TIC-1, . . . , TIC-N respectively corresponding to N captured images CI-1, . . . , CI-N may be displayed.

The N marker time-intensity curves TIC-1, ..., TIC-N respectively display capture time sections T1, ..., TN of corresponding captured images CI-1, ..., CI-N among the N captured images CI-1, ..., CI-N based on a group time-intensity curve TIC-G. Alternatively, unlike in FIG. 10, N marker time-intensity curves TIC-1, ..., TIC-N may respectively display capture time points instead of the capture time sections T1, ..., TN.

Figure 11:
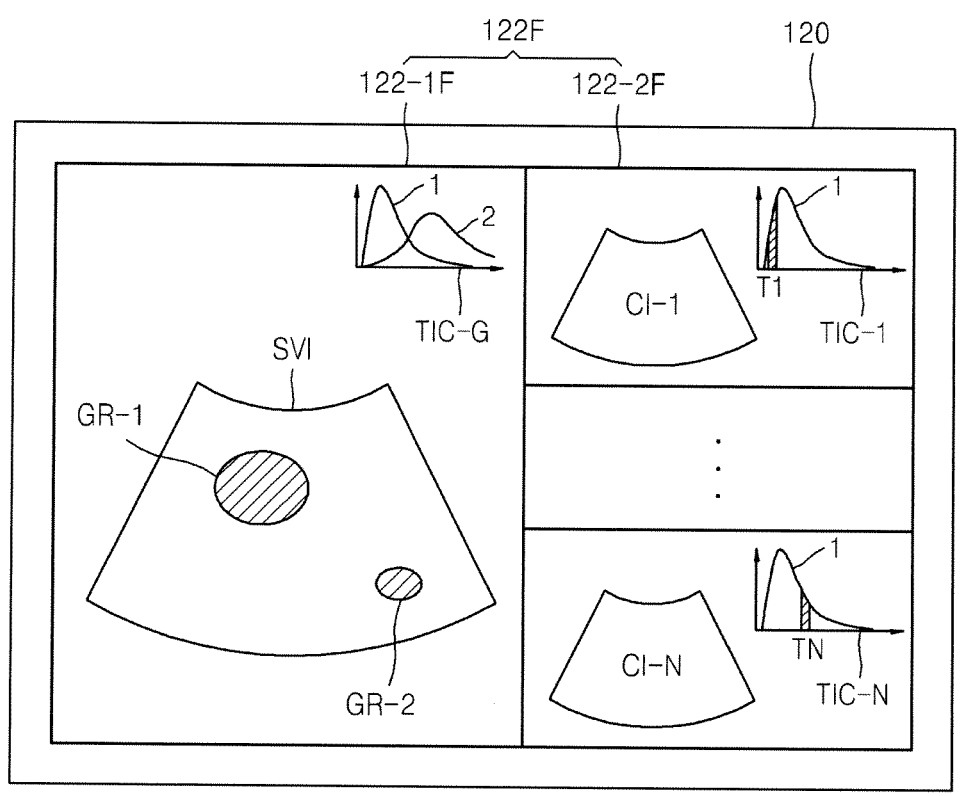
FIG. 11 is a schematic view of a screen of a display unit of FIG. 1 according to another embodiment of the present invention.

FIG. 11 is a schematic view of a screen 122F of the display unit 120 of FIG. 1 according to another embodiment of the present invention. The description of the screen 122E of FIG. 10 may be applied to the screen 122F of FIG. 11, and thus, the following description will focus on differences from the screen 122E of FIG. 10.

Referring to FIGS. 1 and 11, the screen 122F of the display unit 120 may include a first region 122-1F and a second region 122-2F. The control unit 130 may select one of time-intensity curves 1 and 2 of M groups GR-1 and GR-2 included in the group time-intensity curve TIC-G as a selected time-intensity curve. In FIG. 11, it is assumed that the time-intensity curve 1 of the first group GR-1 is selected as a selected time-intensity curve. For example, the control unit 130 may determine the time-intensity curve 1 whose peak point is the fastest among the time-intensity curves 1 and 2 of the M groups GR-1 and GR-2, as a selected time-intensity curve.

N marker time-intensity curves TIC-1, ..., TIC-N displayed on the second region 122-2F may indicate capture time sections T1, ..., TN of corresponding captured images CI-1, ..., CI-N among the N captured images displayed on the selected time-intensity curve 1.

Referring to FIG. 1 and FIG. 9 through FIG. 11 again, the control unit 130 may obtain the M groups GR-1 and GR-2 as ROIs, and the display unit 120 may display a scan video image SVI and N captured images CI-1, ..., CI-N captured from the scan video image SVI as illustrated in FIGS. 9 through 11.

The N captured images CI-1, ..., CI-N may be obtained upon user request. The user request may be input via the input unit 150.

Alternatively, N captured images CI-1, ..., CI-N may be captured by the control unit 130 irrespective of a user request. For example, the control unit 130 may periodically capture a scan video image to obtain N captured images CI-1, ..., CI-N. For another example, the control unit 130 may obtain N captured images CI-1, ..., CI-N based on a group time-intensity curve TIC-G. The control unit 130 may divide the scan video image SVI into N phases based on the group time-intensity curve TIC-G, and may capture the scan video image SVI from each of N phases to obtain N captured images CI-1, ..., CI-N. The control unit 130 may divide the scan video image SVI into N phases based on the selected time-intensity curve 1 among the time-intensity curves 1 and 2 of the M groups GR-1 and GR-2 included in the group time-intensity curves TIC-G.

FIG. 12 is a flowchart illustrating a method of operating a diagnostic imaging apparatus according to another embodiment of the present invention.

Referring to FIG. 12, in operation S100, the diagnostic imaging apparatus scans a subject, into which a contrast agent is injected, to obtain a scan signal. In operation S200, the diagnostic imaging apparatus displays a scan video image that is obtained based on the scan signal, on a first region of a screen. In operation S300, the diagnostic imaging apparatus displays N captured images that are captured from the scan video image on a second region of the screen.

FIG. 13 is a flowchart illustrating a method of operating a diagnostic imaging apparatus according to another embodiment of the present invention.

Referring to FIG. 13, in operation S100, the diagnostic imaging apparatus scans a subject, into which a contrast agent is injected, to obtain a scan signal. In operation S200, the diagnostic imaging apparatus displays a scan video image that is obtained based on the scan signal, on a first region of a screen. In operation 210, the diagnostic imaging apparatus may obtain a ROI of the scan video image. In operation S220, the diagnostic imaging apparatus may obtain N captured images from the scan video image. In operation S300, the diagnostic imaging apparatus displays N captured images that are captured from the scan video image on a second region of the screen.

Figure 14:
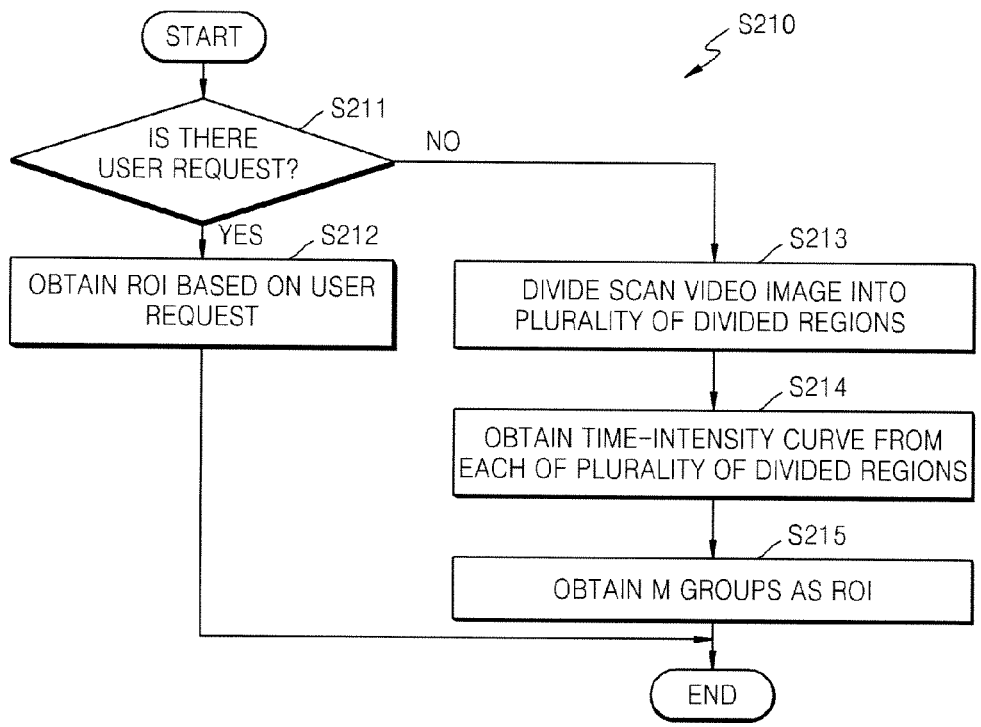
FIG. 14 is a flowchart illustrating an operation of obtaining a ROI of the method of FIG. 13 according to an embodiment of the present invention.

FIG. 14 is a flowchart illustrating an operation S210 of obtaining a ROI of the method of FIG. 13 according to an embodiment of the present invention.

Referring to FIG. 14, the diagnostic imaging apparatus may determine whether there is a user request regarding a ROI or not in operation S211.

If there is a user request, the diagnostic imaging apparatus may obtain a ROI based on the user request in operation S212.

If there is no user request, the diagnostic imaging apparatus may divide the scan video image into a plurality of divided regions in operation S213. In operation S214, the diagnostic imaging apparatus may obtain a time-intensity curve for each of the plurality of divided regions to obtain a plurality of divided time-intensity curves. In operation S215, the diagnostic imaging apparatus may obtain M groups based on the plurality of divided time-intensity curves to obtain the M groups as ROIs.

Figure 15:
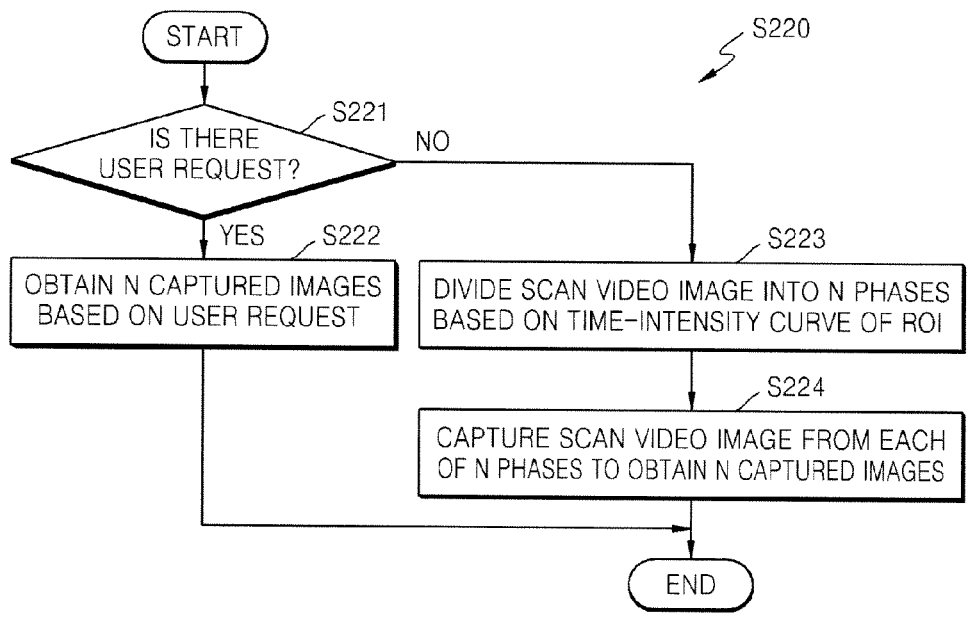
FIG. 15 is a flowchart illustrating an operation of obtaining N captured images of the method of FIG. 13 according to an embodiment of the present invention.

FIG. 15 is a flowchart illustrating an operation S220 of obtaining N captured images of the method of FIG. 13 according to an embodiment of the present invention.

Referring to FIG. 15, the diagnostic imaging apparatus may determine whether there is a user request regarding capturing in operation S221. The user request regarding capturing may be in regard to a capture time point or a capture time section.

If there is a user request, the diagnostic imaging apparatus may obtain N captured images from a scan video image based on the user request in operation S222.

If there is no user request, the diagnostic imaging apparatus may divide a scan video image into N phases based on a time-intensity curve of a ROI in operation S223. The diagnostic imaging apparatus may capture a scan video image from each of N phases to obtain N captured images in operation S224.

The methods illustrated in FIGS. 12 through 15 may be performed in the diagnostic imaging apparatus of FIG. 1. The description with reference to FIGS. 1 through 11 may apply to the operations of the methods. Thus, redundant descriptions will be omitted.

As described above, according to the embodiments of the present invention, an efficient diagnostic imaging apparatus and a method of efficiently operating the same may be provided.

According to the diagnostic imaging apparatus according to the embodiments of the present invention, a scan video image and N captured images captured from the scan video image are simultaneously displayed so as to provide a user with diagnosis convenience. In addition, diagnosis speed may be improved by using the diagnostic imaging apparatus.

In addition, according to the diagnostic imaging apparatus according to the embodiments of the present invention, a time-intensity curve of a ROI of a scan video image may be displayed. When diagnosing whether a ROI is a cancer tissue or not, the time-intensity curve of the ROI may be for the user an objective standard for diagnosis. Thus, diagnosis accuracy may be increased.

The ROI may be determined upon a user request or irrespective of a user request. Capture time points or capture time sections of N captured images may be determined upon a user request or irrespective of a user request. Accordingly, user convenience may be achieved when the user operates the diagnostic imaging apparatus.

According to the embodiments of the present invention, an efficient diagnostic imaging apparatus and a method of efficiently operating the apparatus may be provided.

The embodiments of the present invention can be written as computer programs and can be implemented in general-use digital computers that execute the programs using a computer readable recording medium. In addition, data structures used in the methods described above may be written to computer readable recording media using various means. Examples of the computer readable recording medium include magnetic storage media (e.g., read-only memory (ROM), random-access memory (RAM), universal serial buses (USBs), floppy disks, hard disks, etc.), optical reading medium (e.g., CR-ROMs, DVDs, etc.), and PC interfaces (e.g., PCI, PCI-express, Wifi, etc.).

While this invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A diagnostic imaging apparatus, comprising:
   a probe that scans a subject into which a contrast agent is injected, to obtain a scan signal; and
   a display unit that displays a scan video image obtained based on the scan signal, on a first region of a screen, and N captured images from the scan video image in order of time on a second region of the screen, where N is a natural number,
   wherein the display unit displays N marker time-intensity plots respectively corresponding to the N captured images on the second region, each of the N marker time-intensity plots includes a same reference time-intensity curve which is a time-intensity curve of a region of interest (ROI) in the scan video image, and each of the N marker time-intensity plots indicates a respective capture time point or respective capture time section of a corresponding captured image among the N captured images on the reference time-intensity curve.

2. The diagnostic imaging apparatus of claim 1, wherein the display unit displays the reference time-intensity curve on the first region.

3. The diagnostic imaging apparatus of claim 2, wherein the N captured images are obtained based on a user request.

4. The diagnostic imaging apparatus of claim 2, further comprising a control unit that divides the scan video image into N phases based on the reference time-intensity curve, and captures the scan video image from each of the N phases to obtain the N captured images.

5. The diagnostic imaging apparatus of claim 2, wherein the ROI is obtained based on a user request.

6. The diagnostic imaging apparatus of claim 1, further comprising a control unit that divides the scan video image into a plurality of divided regions, obtains a plurality of divided time-intensity curves which are respectively time-intensity curves of the plurality of divided regions, and obtains M groups based on the plurality of divided time-intensity curves,
   wherein the M groups each include at least one among the plurality of divided regions, and M is a natural number.

7. The diagnostic imaging apparatus of claim 6, wherein the display unit displays the M groups on the scan video image.

8. The diagnostic imaging apparatus of claim 7, wherein the display unit displays a group time-intensity curve including a time-intensity curve of each of the M groups, on the first region.

9. The diagnostic imaging apparatus of claim 8, wherein the N captured images are obtained based on a user request.

10. The diagnostic imaging apparatus of claim 8, wherein the control unit divides the scan video image into N phases based on the group time-intensity curve, and captures the scan video image from each of the N phases to obtain the N captured images.

11. A method of operating a diagnostic imaging apparatus, the method comprising:
    scanning a subject, into which a contrast agent is injected, to obtain a scan signal;
    displaying a scan video image that is obtained based on the scan signal, on a first region of a screen; and
    displaying N captured images captured from the scan video image in order of time, on a second region of the screen, where N is a natural number, and N marker time-intensity plots respectively corresponding to the N captured images on the second region,
    wherein each of the N marker time-intensity plots includes a same reference time-intensity curve which is a time-intensity curve of a region of interest (ROI) in the scan video image, and each of the N marker time-intensity plots indicates a respective capture time point or respective capture time section of a corresponding captured image among the N captured images on the reference time-intensity curve.

12. The method of claim 11, further comprising:
    obtaining a region of interest (ROI) of the scan video image; and
    obtaining the N captured images from the scan video image.

13. The method of claim 12, wherein the obtaining of the ROI comprises:
    determining whether there is a user request regarding the ROI; and
    if there is a user request, obtaining the ROI based on the user request.

14. The method of claim 13, wherein the obtaining of the ROI further comprises:
    dividing the scan video image into a plurality of divided regions if there is no user request;
    obtaining a time-intensity curve from each of the plurality of divided regions to obtain a plurality of divided time-intensity curves; and
    obtaining M groups based on the plurality of divided time-intensity curves, and obtaining the M groups as the ROI,
    wherein the M groups each include at least one from among the divided regions, and M is a natural number.

15. The method of claim 14, further comprising displaying a time-intensity curve of the ROI on the first region of the screen.

16. The method of claim 12, wherein the obtaining of the N captured images comprises:
   determining whether there is a user request regarding a capture time point or a capture time section; and
   if there is a user request, obtaining the N captured images from the scan video image based on the user request.

17. The method of claim 16, wherein the obtaining of the N captured images further comprises:
   if there is no user request, dividing the scan video image into N phases based on a time-intensity curve of the ROI; and
   obtaining N captured images by capturing the scan video image from each of the N phases.

18. A non-transitory computer-readable recording medium having embodied thereon a program for implementing the method of operating a diagnostic imaging apparatus of claim 11.

* * * * *